United States Patent [19]
Kraus et al.

[11] Patent Number: 5,071,961
[45] Date of Patent: * Dec. 10, 1991

[54] METHOD OF ENRICHMENT OF COAGULATION FACTORS II, VII, IX AND X

[75] Inventors: Michael Kraus, Frankfurt; Wolfgang Möller, Oberursel; Bertram Eichentopf, Bad Soden, all of Fed. Rep. of Germany

[73] Assignee: Biotest Pharma GmbH, Dreieich, Fed. Rep. of Germany

[*] Notice: The portion of the term of this patent subsequent to Oct. 29, 2008 has been disclaimed.

[21] Appl. No.: 383,371

[22] Filed: Jul. 20, 1989

[30] Foreign Application Priority Data

Aug. 6, 1988 [DE] Fed. Rep. of Germany ....... 3826792

[51] Int. Cl.$^5$ .......................... C07K 3/02; C07K 3/22
[52] U.S. Cl. .................... 530/384; 530/381; 530/416
[58] Field of Search ............... 530/380, 381, 384, 416; 424/101

[56] References Cited

U.S. PATENT DOCUMENTS 4,481,189  11/1984  Prince ................................. 424/101

OTHER PUBLICATIONS

CA107:161669t Smith, K. J. (Blood Systems, Inc.) Eur. Pat. Appln. EP229,026 15 Jul. 1987. Matsumoto et al. (1980) J. Biochem. 87, 535-540.

Primary Examiner—Garnette D. Draper
Assistant Examiner—R. Keith Baker
Attorney, Agent, or Firm—Sprung Horn Kramer & Woods

[57] ABSTRACT

A method of enrichment of coagulation Factors II, VII, IX and X in preparations obtained from plasma, plasma fractions, or other liquids containing the factors, by adsorbing the factor or factors onto a polymeric matrix that carries an α-hydroxylamine group, and eluting the factors. When the chromatography conditions are appropriate, it is also easy to prepare a highly concentrated Factor IX preparation with a purity of more than 10 U per mg of protein.

13 Claims, No Drawings

METHOD OF ENRICHMENT OF COAGULATION FACTORS II, VII, IX AND X

The invention concerns a method of enrichment of coagulation Factors II, VII, IX and X in preparations obtained from plasma or other fractions by adsorbing the factors onto a matrix that carries an α-hydroxylamine group and eluting the factors in order to obtain preparations of a higher specific activity.

Second to hemophilia A, hemophilia B is the most common hereditary coagulation disorder. The hemophilia-B patient lacks Factor IX, which is essential to coagulation. The disease can, however, be treated by substitution with preparations that contain Factor IX. Other fields of application for Factors II, VII, IX and X are such acquired coagulation disorders as disseminated intravascular coagulation subsequent to polytraumatization or the lack of vitamin-K dependent factors that accompanies liver diseases.

Until 1954, the only available means of treating a lack of Factor IX was fresh-frozen plasma. Attempts were made in subsequent years to enrich Factor IX by adsorption onto barium sulfate (Aggeler, P. M. et al., Trans. 6th Congress, Internat. Soc. Hematol., N.Y., Grune & Stratton, 1956, 490-97) or tricalcium phosphate (Janiak and Soulier, Thromb. et Diath. Haemorrh. 8 [1962], 406-24).

The adsorption of Factor IX onto such mineral adsorbents as calcium phosphate, barium sulfate, aluminum hydroxide, and hydroxyapatite for example was further optimized over the years and is described in European Patent 56 629 for example. The specific activity cited therein for Factor IX is 2.5 U per mg of protein. The same preparation contained 2.0 U of Factor II, 1.0 U of Factor VII, and 2.5 U of Factor X per mg of protein. Factors II, VII, IX and X are also called PPSB complex.

DEAE anion-exchange chromatography has also been used since 1965 (Tullis et al, New Engl. J. Med. 273 [1965], 667-74) to isolate Factor IX or PPSB complex. An optimized method of isolating PPSB complex by adsorption onto DEAE Sephadex is described in European Patent 41 174, wherein the specific activity of Factor IX is 2.2 U per mg of protein, accompanied by a severe impoverishment in Factor VII.

Factor IX preparations are now employed either in the form of a PPSB complex with varying proportions of Factors II, VII, IX, and X or in that of a highly enriched Factor IX concentrate for treating coagulation disorders.

When all four PPSB factors must be present in the Factor IX preparation in approximately the same proportion, adsorbing them from plasma at the current state of the art results in a product with a specific activity of around 1 U per mg of protein for all the factors, except an expensive multistage purification method, with a correspondingly low yield, is employed.

Prothromplex S-TIM 4 (Immuno), which is currently the most highly enriched commercially available PPSB product, can be provided with a specific activity of more than 1 U per mg of protein for all four factors only by purifying the Factor VII separately and then mixing it into the PPSB complex. Highly enriched Factor IX concentrates with a specific activity of more than 10 U per mg of protein for Factor IX can be obtained at the current state of the art only by fractionating them from plasma in several stages. Examples are described in International Patent Application WO 83/03760 or in German 3 101 752.

The object of the present invention is to provide a simple method of obtaining a Factor IX preparation with a specific activity of more than 1 U per mg of protein for Factor IX and optionally containing the other PPSB factors, II, VII and X, in approximately the same proportion.

This object is attained in accordance with the invention by treating plasma or another fraction that contains the coagulation factors with a matrix that carries an α-hydroxylamine group, adsorbing the Factor IX, and optionally the Factors II, VII and X, washing with appropriate buffers, and eluting the factors. The matrix that carries the α-hydroxylamine group can be prepared by the method known from I. Matsumoto et al., J. Biochem. 87 (1980), 535-40.

It has surprisingly been discovered that, depending on the ionic strength of the solution, the Factor IX or the total PPSB complex will rapidly be bound at a high yield and can be eluted out again at high purity.

The use of gels with alkylamine groups but without an α-hydroxylamine group to purify Factor VIII is known from the literature (Thromb. Haemostas. [Stuttgart] 47, 2 [1982], 124-27; EP 0 144 957; British Journal of Haematology 43 [1979], 669-74). These gels also bind the PPSB factors. Adsorption follows approximately the same rules as in the case of Factor VIII.

The adsorptive behavior of such known gels (Sepharose), which have carbon chains of various lengths between the matrix and the terminal amine group, was tested in comparison with that of a gel with an α-hydroxylaminopropyl group (α-Hydroxylaminopropyl Sepharose). 50 ml each of citrated plasma were diluted 1:3 with water and chromatographed over 1×5 cm columns packed with various gels. The content of unbound coagulation factors in the residual plasma was determined subsequent to adsorption and is shown in Table 1 in percent of activity of the starting plasma.

TABLE 1

Remaining content of PPSB factors in plasma subsequent to adsorption on Amino Sepharose

| | Factor: | | | | |
|---|---|---|---|---|---|
| | II | VII | VIII | IX | X |
| Aminoethyl Sepharose | 99 | 97 | 93 | 97 | 98 |
| Aminopropyl Sepharose | 94 | 99 | 92 | 95 | 96 |
| Aminopentyl Sepharose | 11 | 22 | 7 | 10 | 16 |
| Aminohexyl Sepharose | 1 | 3 | 4 | 2 | 1 |
| Aminooctyl Sepharose | 4 | 2 | 4 | 4 | 3 |
| α-hydroxylaminopropyl Sepharose (invention) | 6 | 2 | 86 | 3 | 3 |

As will be evident from Table 1, the optimum conditions for such adsorption onto amino-alkyl carriers that lack the α-hydroxylamine group occur when what is called the spacer has a chain 6 to 8 carbon atoms long. The purity of the PPSB factors subsequent to chromatography with Aminohexyl Sepharose is more or less comparable with, the specific activity subsequent to chromatography with a DEAE matrix.

Preparation of carriers with amine groups from a preliminary epoxy stage with ammonia results, in addition to the amino group, in an α-hydroxyl group. It was, due to the aforesaid results for pure alkylamine carriers, surprising to discover that α-hydroxylamine carriers exhibit a completely different behavior in relation to binding the PPSB factors.

In contrast to what occurs with the alkylamine carriers, a spacer with 6 to 8 carbon atoms is no longer needed. Even α-hydroxylamine groups on a spacer with 3 carbon atoms lead to powerful adsorption of the PPSB factors.

The PPSB factors are substantially more specifically adsorbed and subsequently eluted at greater purity than has previously been possible with alkylamine carriers and DEAE anion exchangers.

Adsorption onto α-hydroxylamine carriers is substantially more rapid than onto DEAE anion exchangers, which have up to now constituted the most frequent medium. Whereas it takes around 1 to 4 hours to adsorb Factors II, VII, IX and X onto DEAE Sepharose, the process is complete in as few as 5 minutes when the α-hydroxylaminopropyl gels in accordance with the invention are employed in comparable test apparatus.

Another difference from the known DEAE anion-exchange chromatography is the highly satisfactory binding of Factor VII to the α-hydroxylamine matrix at low ionic strength and the joint elution of all PPSB factors at a high and approximately equal specific activity of more than 1 U per mg of protein. In DEAE anion-exchange chromatography, the attainment of such high specific activities has always necessarily been accompanied by the loss of a considerable amount of Factor VII. In practice, this has meant that the Factor VII was either present at a very low level in such highly purified PPSB concentrates or that it had to be prepared separately and added.

The PPSB factors are preferably adsorbed onto the α-hydroxylamine carriers in accordance with the invention at a pH of 7.0 to 7.5 and at a conductivity of less than 7.5 mS/cm. The PPSB factors can be eluted with 0.25 to 1M of sodium chloride at a yield of up to 80% of their starting activity.

The starting material can be plasma, plasma fractions, or other solutions that contain the coagulation factors.

The method in accordance with the invention can also be employed to obtain or enrich individual PPSB Factors II, VII and X if the starting solutions contain only a single factor.

In addition to such enriched PPSB or a preparation containing the aforesaid individual factors, the α-hydroxylamine carriers in accordance with the invention can also be employed to prepare a high purity Factor IX concentrate from plasma or plasma fractions subject to appropriate chromatography conditions. When plasma or plasma fractions are adsorbed at a slightly higher conductivity, preferably 12 to 15 mS/cm, and at a pH of preferably 4.5 to 7.7, the Factor IX in particular will bind even more specifically to the matrix and can be eluted at a purity of 10 to 20 U per mg of protein. It has previously been possible to obtain such specific activities only with multistage processes and at yields of considerably less than the 30 to 40% that can be attained in accordance with the invention. Adsorbing Factors II, VII, IX and X onto α-hydroxylamine carriers accordingly represents a considerable advance in the technical harvesting of both coagulation Factor IX and PPSB complex. The advantages are higher yield and higher purity by way of a simple and rapid process.

The adsorption of the coagulation factors is not confined to column chromatography but can also be carried out in batch. Due to the extraordinarily rapid binding of the factors to the matrix, the method in accordance with the invention is also appropriate for affinity separation through membranes when a membrane modified with α-hydroxylamine groups is employed to adsorb the factors.

Factors II, VII or X can also be purified to the corresponding high concentrates from appropriately preliminarily purified or enriched solutions. Before or after the factors are adsorbed onto the α-hydroxylamine matrix, they can be sterilized with β-propiolactone and/or ultraviolet light, with solvents and detergents, or by pasteurization in order to inactivate any human-pathogenic viruses.

The invention will now be described with reference to the following examples.

EXAMPLE 1

A 25 ml column with a matrix that carries α-hydroxylaminopropyl aminopropyl ligands and consists of a copolymer of glycidyl methacrylate, pentaerythritol dimethacrylate, and polyvinyl alcohol (Fraktogel-TSK-Amino, Merck, Darmstadt) was equilibrated with 100 ml of buffer B (10 mM citrate, pH 7.0).

350 ml of citrated plasma were diluted to a conductivity of 7 mS/cm and transferred to the column at a flow rate of 300 ml/h. The column was then washed with 100 ml of buffer B. The PPSB factors were eluted with 0.5M of sodium chloride in buffer B. The yield of PPSB factors was 60 to 80% of the initial activity. The specific activities of the PPSB factors were 2.1 U of Factor II, 1.9 U of Factor VII, 2.3 U of Factor IX, and 2.0 U of Factor X per mg of protein.

EXAMPLE 2

A 20 ml column of the adsorbent described in Example 1 was equilibrated with 50 ml of buffer A (10 mM of citrate, 10 mM of $Na_2HPO_4$, and 100 mM of NaCl, at a pH of 7.5). 1000 ml of plasma with a conductivity of 13 mS/cm were added at a flow rate of 300 ml/h and washed with 150 ml of buffer A. The Factor IX was eluted with a linear gradient of 0 to 0.5M of sodium chloride in buffer A, which also contained 0.5 U/ml of AT III and 5 U/ml of heparin.

The contents of Factor IX and protein were determined in the fractions.

The fractions with a specific activity of more than 5 U of Factor IX per mg of protein were pooled. The result was a Factor IX concentrate that exhibited a specific activity of 15 U of Factor IX per mg of protein. The yield was 40% of the initial activity in the plasma.

EXAMPLE 3

200 ml each of plasma were chromatographed as described in Example 1 on various carriers carrying the α-hydroxylamine group. The α-hydroxylamine group was attached to the matrix according to the method of I. Matsumoto et al., *J. Biochem* 87 (1980), 535–40. The carriers were:

1. copolymer of vinyl acetate and divinylethylene urea (e.g. Biosynth)
2. copolymer of methacrylamide, N-methylene-bis-methacrylamide, and allylglycidyl ether (e.g. Eupergit)
3. polymers of carbohydrates (e.g. Sepharose).

The results were in principle identical with those obtained in Example 1 and are listed in Table 2.

TABLE 2

| Carrier | Yield, % | | | | Spec. act., U/mg | | | |
| --- | --- | --- | --- | --- | --- | --- | --- | --- |
| | Factor: | | | | | | | |
| | II | VII | IX | X | II | VII | IX | X |
| 1 | 50 | 82 | 55 | 61 | 1.5 | 2.1 | 1.5 | 1.7 |
| 2 | 57 | 70 | 54 | 48 | 1.6 | 2.0 | 1.8 | 1.5 |
| 3 | 52 | 43 | 57 | 46 | 1.2 | 1.0 | 1.3 | 1.1 |

EXAMPLE 4

1000 ml of plasma were treated overnight with 0.25% β-propiolactone at a pH of 8.0 and then irradiated with ultraviolet light. The cold-sterilized plasma was processed as described in Example 1. At a yield of 60 to 80%, the purity of the PPSB factors was comparable to the specific activity cited in Example 1.

EXAMPLE 5

100 ml of a commercial PPSB product with a specific activity of 0.6 U of Factor IX per mg of protein were chromatographed as described in Example 2 through 30 ml of the adsorbent described in Example 1. It was possible to isolate a high Factor IX concentrate with 10.4 U per mg of protein at a yield of 95%.

It will be understood that the specification and examples are illustrative but not limitative of the present invention and that other embodiments within the spirit and scope of the invention will suggest themselves to those skilled in the art.

What is claimed is:

1. A method of enrichment of at least one of coagulation Factors II, VII, IX and X, comprising contacting a solution containing such factor with an adsorbent that carries an α-hydroxylaminopropyl group thereby to adsorb such factor, and then eluting the factor.

2. A method according to claim 1, wherein the starting solution is plasma or a plasma fraction containing the factor.

3. A method according to claim 1, wherein the adsorbent carrying the α-hydroxylaminopropyl group is an organic polymer.

4. A method according to claim 3, wherein the polymer is a copolymer of glycidyl methacrylate, pentaerythritol dimethacrylate and polyvinyl alcohol.

5. A method according to claim 3, wherein the polymer is a copolymer of methacrylamide, N-methylenebismethacrylamide and allylglycidyl ether.

6. A method according to claim 3, wherein the polymer is a copolymer of vinyl acetate and divinylethylene urea.

7. A method according to claim 3, wherein the polymer is a α-hydroxylaminopropyl-Sepharose.

8. A method according to claim 1, wherein the adsorbent carrying the α-hydroxylaminopropyl group is an inorganic polymer.

9. A method according to claim 8, wherein the inorganic polymer is a silicate matrix.

10. A method according to claim 1, wherein the adsorption is effected by means of column chromatography, batch by batch, or on a membrane.

11. A method according to claim 1, including treating the factor-containing solution to inactivate any viruses present therein.

12. The method according to claim 11, wherein the virus-inactivation is effected by β-propiolactone or ultraviolet light, by solvents and/or detergents, or by pasteurization before or after the factors are adsorbed onto the carrier.

13. A method of enrichment of coagulation Factor IX in a solution containing it, comprising contacting such solution with an adsorbent that carries an α-hydroxylaminopropyl group, the solution having a conductivity of about 12 to 15 mS/cm and a pH of about 4.5 to 7.7, thereby to adsorb and hold the Factor IX preferentially, and then eluting the Factor IX.

* * * * *

UNITED STATES PATENT AND TRADEMARK OFFICE
CERTIFICATE OF CORRECTION

PATENT NO. : 5,071,961

DATED : December 10, 1991

INVENTOR(S) : Kraus et al.

It is certified that error appears in the above-identified patent and that said Letters Patent is hereby corrected as shown below:

Col. 6, line 31    Delete " and/or " and substitute -- or --

Signed and Sealed this

Sixth Day of July, 1993

Attest:

MICHAEL K. KIRK

*Attesting Officer*     Acting Commissioner of Patents and Trademarks